United States Patent [19]

Okumura et al.

[11] Patent Number: 4,908,373
[45] Date of Patent: Mar. 13, 1990

[54] 1-[2-(4-HYDROXYBENZOYL)ETHANOYL]-2-PIPERIDONE AND A PROCESS FOR PRODUCTION AS WELL AS ALCOHOL FERMENTATION PROMOTER CONTAINING THE SAME AS EFFECTIVE INGREDIENT

[75] Inventors: Minoru Okumura, Kakogawa; Yoshio Maekawa, Miki; Hironori Mizuno; Osamu Yagiyu, both of Kakogawa, all of Japan

[73] Assignee: Taki Chemical Co., Ltd., Hyogo, Japan

[21] Appl. No.: 340,096

[22] PCT Filed: Apr. 22, 1988

[86] PCT No.: PCT/JP88/00392
§ 371 Date: Dec. 27, 1988
§ 102(e) Date: Dec. 27, 1988

[87] PCT Pub. No.: WO88/08418
PCT Pub. Date: Nov. 3, 1988

[30] Foreign Application Priority Data

Apr. 28, 1987 [JP] Japan .................. 62-106038

[51] Int. Cl.$^4$ .......................... C07D 211/74

[52] U.S. Cl. ................... 514/327; 514/330; 546/221

[58] Field of Search ............... 546/221; 514/327, 330

[56] References Cited

FOREIGN PATENT DOCUMENTS 216133 9/1986 Japan .
242573 10/1986 Japan .
283906 11/1986 Japan .

Primary Examiner—Glennon H. Hollrah
Assistant Examiner—Ba K. Trinh
Attorney, Agent, or Firm—Wenderoth, Lind & Ponack

[57] ABSTRACT

The present invention relates to 1-[2-(4-hydroxybenzoyl)ethanoyl]-2-piperidone which is a novel compound of N-acyl lactam compounds and exhibit excellent effects in promoting fermentation in alcohol fermentation.

This novel compound can be prepared by converting 2-(4-benzyloxybenzoyl)acetic acid into the acid chloride, then coupling the acid chloride with 2-piperidone or an alkylate of 2-piperidone and then subjecting to debenzylation.

3 Claims, No Drawings

1-[2-(4-HYDROXYBENZOYL)ETHANOYL]-2-PIPERIDONE AND A PROCESS FOR PRODUCTION AS WELL AS ALCOHOL FERMENTATION PROMOTER CONTAINING THE SAME AS EFFECTIVE INGREDIENT

FIELD OF THE INVENTION

The present invention relates to 1-[2-(4-hydroxybenzoyl)ethanoyl]-2-piperidone represented by structural formula (I):

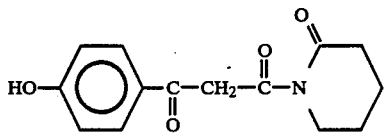

and a process for production as well as an alcohol fermentation promoter containing the same as effective ingredient.

BACKGROUND

Alcohol fermentation is known from old in fermentation of alcohols such as Japanese sake, beer, wine, etc. In recent years, the alcohol fermentation has also been applied to preparation of energy alcohol as biofuel, as a substitute for petroleum.

In alcohol fermentation as biofuel, fermentation should efficiently be performed using inexpensive starchy raw materials from a standpoint of preparation of alcohol fuel and, survey of cheap raw materials of development and investigations on excellent various yeasts have been extensively made.

On the other hand, development has also been made from fermentation engineering, in which yeast cells are immobilized to prepare alcohol continuously and efficiently.

However, these techniques are all insufficient for improving fermentation efficiency to such an extent that they could achieve any economical effect. Under the actual situation, alcohol fermentation as biofuel still remains at the stage of research.

The present inventors previously began to work on physiologically active substances for plant, synthesized a variety of compounds and found that N-acyl lactam compounds were excellent as active substances (Japanese Patent Application Laid Open No. 61-246105). As a result of further investigations, they have found that 1-[2-(4-hydroxybenzoyl)ethanoyl]-2-piperidone of the present invention, which is a novel N-acyl lactam compound, shows an excellent fermentation promotive capacity and have accomplished the present invention, based on such a finding.

DISCLOSURE OF THE INVENTION

That is, the present invention relates to 1-[2-(4-hydroxybenzoyl)ethanoyl]-2-piperidone represented by structural formula (I):

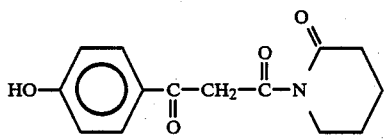

and a process for production as well as an alcohol fermentation promoter containing the same as effective ingredient.

1-[2-(4-Hydroxybenzoyl)ethanoyl]-2-piperidone of the present invention is a novel compound and exhibits as an alcohol fermentation promoter an excellent fermentation promoting effect that is hitherto unknown.

Hereafter the present invention will be described in detail.

1-[2-(4-Hydroxybenzoyl)ethanoyl]-2-piperidone of the present invention is a novel compound, which structural formula (I) is represented by:

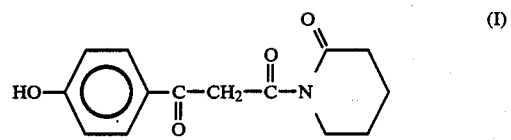

A process for producing the compound is described below. The compound can be prepared by converting a compound represented by structural formula (II):

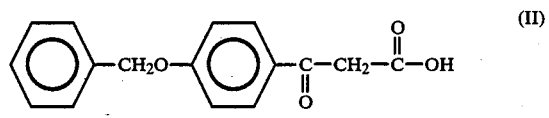

into the acid chloride, then coupling the acid chloride with 2-piperidone or an alkylate of 2-piperidone and then subjecting to debenzylation.

This compound (II) can be obtained, for example, by the following process. Firstly, using methyl 4-hydroxybenzoate, the hydroxyl group is benzylated with benzyl chloride to obtain methyl 4-benzyloxybenzoate. Next, the benzylated compound is hydrolyzed to obtain 4-benzyloxybenzoic acid. The acid is converted into the acid chloride to give 4-benzyloxybenzoyl chloride. 4-Benzyloxybenzoyl chloride is reacted with monoanion of bistrimethylsilyl malonate and water is added to the reaction product to effect hydrolysis and decarbonation, whereby the compound represented by structural formula (II) can be obtained. The reaction in this case may be carried out in a manner described in J. W. F. K. Barnick et al., Synthesis, No. 10, 787–788 (1979).

The compound (II) which can readily be obtained by such a well known process is then provided to the reaction of converting into the acid chloride.

For conversion into the acid chloride, thionyl chloride, phosphorus pentachloride, phosphorus trichloride, oxalyl chloride, etc. can be used, but in view of preventing formation of by-products, it is desired to use oxalyl chloride.

Further as a solvent used in this case, dry benzene and dry tetrahydrofuran (hereafter simply referred to as THF) are desired to prevent formation of by-products.

Next, coupling is carried out using 2-piperidone or alkylates of 2-piperidone.

As the alkylate of 2-piperidone, mention may be made of, for example, N-trimethylsilyl-2-piperidone obtained by trimethylsilylating 2-piperidone.

In these reactions, in order to avoid formation of by-products, the reaction should be conducted at room temperature or at a lower temperature.

By this coupling, 1-[2-(4-hydroxybenzoyl)ethanoyl]-2-piperidone can be obtained.

Next, this 1-[2-(4-hydroxybenzoyl)ethanoyl]-2-piperidone is subjected to debenzylation. Upon the debenzylation, it is preferred to adopt catalytic reduction for the reaction and perform the reaction under mild conditions, because the amide binding site of the compound is unstable to acid and alkali.

Further as the catalyst used in this catalytic reduction, various catalysts for reduction can be used but in order to perform reduction under mild conditions, it is desired to use palladium catalysts, for example, palladium-barium sulfate which catalytic action is weakened.

With respect to the reaction temperature, it is desired that the reaction be carried out at temperatures lower than room temperature, in view of stability of the compound described above. The reaction time varies depending upon reaction temperature, kind of catalyst used, etc. but is generally for about 2 hours at 15° C. in the case of using 5% palladium-barium sulfate catalyst.

The thus prepared compound of the present invention has excellent fermentation promoting effects in alcohol fermentation that are hitherto unknown.

The compound of the present invention is used as an alcohol fermentation promoter generally be adding the compound to a tank in which fermentation is performed. Alternatively, the compound may also be previously incorporated into raw materials for alcohol fermentation.

The compound of the present invention is an oily substance and may also be dissolved in a solvent such as ethanol, etc. and the resulting solution may be provided for use.

A ratio used varies depending upon kind of yeast cell used in the alcohol fermentation, raw materials used, choice of raw substrate concentration, etc. but is not particularly limited; however, in the batch system, the ratio is generally in the range of 0.00001 to 0.001 w/v% based on an amount of fermentation solution.

in case that mode of fermentation is different, it is desired to perform pre-test and determine the optimum amount to be used.

(EXAMPLES)

Hereafter the present invention will be further described by referring to the examples but is not deemed to be limited thereto.

Further, % is all by weight unless otherwise indicated.

EXAMPLE 1

In a reaction flask of 500 ml volume equipped with a cooler with a calcium chloride tube, 300 ml of dimethylformamide was charged and 15.2 g of methyl 4-hydroxybenzoate and 14.0 g of potassium carbonate were added thereto with stirring. Further, 13.0 g of benzyl chloride was added to the mixture to dissolve therein.

The solution was reacted at 80° C. for 5 hours. After completion of the reaction, dimethylformamide was distilled off and 300 ml of water was added to the residue. The precipitates formed were taken by suction to give 23.6 g of white crystalline methyl 4-benzyloxybenzoate.

After dissolving the benzoate in 500 ml of methanol, the solution was transferred to a reaction flask of 1000 ml volume equipped with a cooler and 30.0 ml of 30% aqueous potassium hydroxide solution was added thereto. The reaction was carried out at a temperature of 80° C. for 10 hours under reflux.

After completion of the reaction, methanol was distilled off and 500 ml of water was added to the system. Furthermore, conc. hydrochloric acid was dropwise added to the mixture to render pH of the solution 1. After filtration by suction, the formed white precipitates were washed several times with water to give 21.0 g of 4-benzyloxybenzoic acid.

Next, 11.4 g of this 4-benzyloxybenzoic acid was charged in a flask of 200 ml volume equipped with a calcium chloride tube and 50 ml each of dry THF and dry benzene were added. In addition, 10.0 g of oxalyl chloride was added to the mixture followed by reacting at room temperature for 12 hours with stirring.

After the reaction, THF, benzene, the unreacted oxalyl chloride and the gas generated were removed under reduced pressure to give 12.0 g of 4-benzyloxybenzoyl chloride.

Separately, 10.4 g of malonic acid and 150 ml of dry benzene were charged in a reaction flask of 500 ml volume equipped with a cooler with a calcium chloride tube and, while stirring, 22.2 g of dry triethylamine was slowly added to the mixture through a dropping funnel at room temperature. After malonic acid was dissolved, 22.7 g of trimethylchlorosilane was gradually added to the solution through a dropping funnel.

After completion of the dropwise addition, the reaction was carried out at room temperature for 8 hours with stirring. After the reaction, the reaction solution was suction filtered. After the filtrate was concentrated under reduced pressure, the concentrate was distilled at 94° to 96° C. under reduced pressure to give 19.4 g of bistrimethylsilyl malonate.

In 30 ml of dry diethyl ether was dissolved 5.01 g of this bistrimethylsilyl malonate. The solution was transferred to a flask of 100 ml volume and put on a dry ice-ethanol bath to cool it.

Argon gas was passed through the flask and 13 ml of 16% butyl lithium solution in hexane was dropwise added over about 20 minutes followed by reaction for further 15 minutes with stirring.

After completion of the reaction, the flask was transferred from the dry ice-ethanol bath to an ice bath and a solution of 2.5 g of 4-benzyloxybenzoyl chloride described above in 10 ml of THF was added followed by stirring for 15 minutes.

Then, 300 ml of ice-cooled saturated sodium hydrogencarbonate aqueous solution was added. After vigorously stirring for 10 minutes, the aqueous phase was fractionated by a separating funnel. A diluted sulfuric acid aqueous solution was dropwise added until pH of the solution became 1. Thus white precipitates were obtained.

After washing with water, the precipitates were dried to give 0.9 g of 2-(4-benzyloxybenzoyl)acetic acid.

In order to identify and confirm this compound, its NMR was measured. The results are shown below.

$^1$H-NMR (90 MHz, CDCl$_3$); δ ppm: 2.55 (2H, s, —CO—CH$_2$—), 5.14 (2H, s, Ph—CH$_2$—), 6.94, 7.08 (2H, d, —Ph—), 7.40 (5H, s, Ph—CH$_2$—), 7.87, 8.02 (2H, d, —Ph—).

Next, 0.54 g of this 2-(4-benzyloxybenzoyl)acetic acid was charged in a reaction flask of 100 ml volume equipped with a calcium chlorid tube and 5 ml of dry THF and 5 ml of dry benzene were added thereto to dissolve them.

To the solution was added 0.38 g of oxalyl chloride followed by reacting at room temperature for 2 hours with stirring.

THF, benzene, the unreacted oxalyl chloride and the gas generated were removed under reduced pressure and, a solution of 1.0 g of N-trimethylsiyl-2-piperidone in 10 ml of dry THF was added thereto under ice cooling followed by reacting at room temperature for an hour with stirring.

After completion of the reaction, THF was removed under reduced pressure and 30 ml of diethyl ether was added to the residue to sufficiently dissolve the reaction product. Then, the solution was transferred to a separation funnel. After the ethereal layer was fractionated, this ethereal solution was washed in sequence with 50 ml of 1N sodium hydroxide aqueous solution, 50 ml of 1N hydrochloric acid aqueous solution, 50 ml of saturated sodium chloride aqueous solution and 100 ml of water. Then 3 g of anhydrous sodium sulfate was added to dehydrate and diethyl ether was distilled off to give 1.10 g of yellow oily substance. Using silica gel column (eluting solution: chloroform:hexane=7:3), 0.60 g of light yellow oily [2-(4-benzyloxybenzoyl)ethanoyl]-2-piperidone was obtained by fractionation.

In order to identify and confirm this compound, its NMR was measured. The results are shown below.

$^1$H-NMR (90 MHz, CDCl$_3$); δ ppm: 1.85 (4H, m, >N—CH$_2$—CH$_2$—CH$_2$—), 2.50 (2H, m, >N—CO—CH$_2$—), 3.83 (2H, m, >N—CH$_2$—CH$_2$—), 4.53 (2H, s, —CO—CH$_2$—CO—), 5.13 (2H, s, Ph—CH$_2$—O—), 6.96, 7.05 (2H, d, —Ph—), 7.39 (5H, s, Ph—CH$_2$—), 7.85, 7.95 (2H, d, —Ph—).

Next, this compound was dissolved in 100 ml of ethyl acetate. The solution was transferred to a flask of 200 ml volume and 0.1 g of 5% palladium-barium sulfate was added thereto. The reaction was carried out at 15° C. for 2 hours in hydrogen gas atmosphere under normal pressure.

After completion of the reaction, the reaction mixture was suction filtered and the filtrate was transferred to a separating funnel. After washing several times with 100 ml of water, 3 g of anhydrous sodium magnesium was added to dehydrate and ethyl acetate was then distilled off to give 0.40 g of colorless oily compound.

This compound was provided for measurement of mass spectrum, elemental analysis and NMR. From the measurement results described below, it was confirmed that this compound was 1-[2-(4-hydroxybenzoyl)ethanoyl]-2-piperidone in accordance with the present invention.

MS (EIMS), M+ 261.

Elemental analysis: C:64.94%. H: 5.76%. N: 5.37%. O: 23.93%.

$^1$H-NMR (90 MHz, CDCl$_3$); δ ppm: 1.85 (4H, m, >N—CH$_2$—CH$_2$—CH$_2$—), 2.53 (2H, m, >N—CO—CH$_2$—CH$_2$—), 3.85 (2H, m, >N—CH$_2$—CH$_2$—), 4.55 (2H, s, Ph—CO—CH$_2$—), 6.71, 6.85, 7.72, 7.86 (4H, q, —Ph—).

EXAMPLE 2

In an Erlenmeyer's flask of 1 liter volume was charged 500 ml of an aqueous solution (pH 5.0) containing 10% sucrose and 0.05% ammonium sulfate followed by sterilizing at 120° C. for 15 minutes, which was made a substrate for fermentation.

Baker's yeast commercially available (manufactured by Oriental Yeast Co., Ltd., live yeast) was used as seed culture. After the yeast was suspended in a 5-fold dilution of the substrate for fermentation, the suspension was settled at 25° C. for an hour.

The compound of the present invention obtained in Example 1 and 1-[3-(4-hydroxyphenyl)propanoyl]-2-piperidone (Comparative Example) were dissolved in ethanol, respectively to prepare 1 w/v% solution, which were made sample solutions, respectively.

The yeast suspension, 3.5×10$^7$ cells/ml, was inoculated on 500 ml of the substrate for fermentation. After settling at 30° C. for an hour, 0.5 ml each of the sample solutions was added followed by static fermentation at 30° C.

A predetermined amount of the solution was taken out from each of fermentation flasks in every definite time after the onset of fermentation and an ethanol concentration of the fermentation solution was determined by gas chromatography.

The results are shown in Table 1.

TABLE 1

| | Ethanol Concentration (w/v %) | | | | |
|---|---|---|---|---|---|
| | 2 Hours | 4 Hours | 6 Hours | 8 Hours | 24 Hours |
| This Invention | 1.9 | 4.1 | 5.3 | 6.5 | 6.9 |
| No addition | 1.8 | 3.4 | 4.1 | 4.6 | 5.0 |
| 1-[3-(4-Hydroxyphenyl)propanoyl]-2-piperidone | 1.8 | 3.5 | 4.0 | 4.5 | 5.0 |

As is clear from Table 1, it is noted that the use of the compound of the present invention results in extremely promoted fermentation.

EXAMPLE 3

In an Erlenmeyer's flask of 100 ml volume with a stopper was charged 50 ml of liquid medium having a composition shown in Table 3.

The compound of the present invention prepared in Example 1 was dissolved in ethanol to make 1 w/v% solution. The solution was made a sample solution, 0.1 ml of which was added to the flask described above.

Various yeasts shown in Table 2 were added to the flask in a cell concentration of 1×10$^8$ cells/ml. After the flask was sealed, ethanol fermentation was performed at a temperature of 30° C. while gently stirring with a magnetic stirrer.

After fermentation was performed for a fixed time period, an ethanol concentration in the fermentation liquid was measured by gas chromatography in a manner similar to Example 2.

For purpose of comparison, fermentation test was carried out in a similar manner using 0.1 ml of ethanol in place of the compound of the present invention.

Test results are shown in Table 4.

TABLE 2

| No. | Yeast Cell |
|---|---|
| (1) | Sacchromyces cerevisiae IAM-4512 |
| (2) | Baker's yeast (Sacchromyces,cerevisiae) |
| (3) | Pachysolen tannophilus IFO-1007 |
| (4) | Candida tropicalis IFO-1402 |

TABLE 3

| | Glucose Substrate | Xylose Substrate |
|---|---|---|
| Substrate concentration | 8.0% | 2.0% |
| Yeast extract | 0.2% | 0.2% |
| NH$_4$Cl | 0.2% | 0.2% |
| K$_2$HPO$_4$ | 0.6% | 0.6% |
| MgSO$_4$.7H$_2$O | 0.03% | 0.03% |
| NaCl | 0.1% | 0.1% |

TABLE 3-continued

|  | Glucose Substrate | Xylose Substrate |
| --- | --- | --- |
| $CaCl_2$ | 0.005% | 0.005% |
| pH | 5.2 | 5.2 |

TABLE 4

| Yeast Cell No. | Yield of Ethanol*1 (%) | |
| --- | --- | --- |
|  | Glucose Substrate*2 | Xylose Substrate*3 |
| This Invention: | | |
| (1) | 63.1 | 1.6 |
| (2) | 59.7 | 41.3 |
| (3) | 31.7 | 21.7 |
| (4) | 61.6 | 48.9 |
| Comparative Example: | | |
| (1) | 37.0 | 0.8 |
| (2) | 25.8 | 17.3 |
| (3) | 15.3 | 12.6 |
| (4) | 41.0 | 23.3 |

*1 The yield of ethanol is shown by a ratio to a theoretical exchange amount.
*2 It shows a yield of ethanol after 24 hours.
*3 It shows a yield of ethanol after 72 hours.

As is clear from Table 4, it is understood that when the compound of the present invention is used, the yield of ethanol increases, in other words, fermentation is promoted, using any type of yeast cells.

We claim:

1. 1-[2-(4-Hydroxybenzoyl)ethanoyl]-2-piperidone represented by structural formula (I):

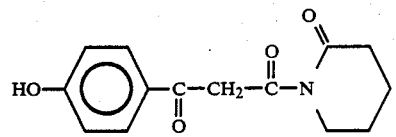

2. A process for producing 1-[2-(4-hydroxybenzoyl)ethanoyl]-2-piperidone represented by structural formula (I):

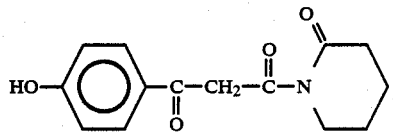

which comprises converting a compound represented by structural formula (II):

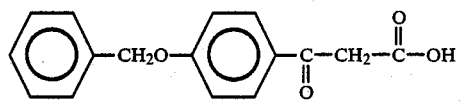

into the acid chloride, then coupling the acid chloride with 2-piperidone or an alkylate of 2-piperidone and then subjecting to debenzylation.

3. An alcohol fermentation promoter comprising as an effective ingredient 1-[2-(4-hydroxybenzoyl)ethanoyl]-2-piperidone represented by structural formula (I):

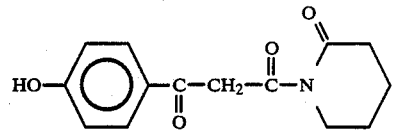

* * * * *